United States Patent [19]
Sullivan

[11] Patent Number: 5,873,718
[45] Date of Patent: Feb. 23, 1999

[54] DENTAL APPARATUS TO REMOVE SALIVA WHILE RETRACTING CHEEKS, LIPS AND TONGUE

[76] Inventor: Terence C. Sullivan, 19720 68$^{th}$ Ave. West, E, Lynnwood, Wash. 98036

[21] Appl. No.: 81,836

[22] Filed: May 19, 1998

[51] Int. Cl.$^6$ ..................................................... A61C 17/04
[52] U.S. Cl. ............................................................ 433/93
[58] Field of Search ................................ 433/91, 93, 94, 433/136, 138, 140

[56] References Cited

U.S. PATENT DOCUMENTS

| | | | |
|---|---|---|---|
| 342,042 | 5/1886 | Rowrey | 433/93 |
| 730,128 | 6/1903 | Jordan | 433/93 |
| 951,130 | 3/1910 | Jordan | 433/93 |
| 4,019,255 | 4/1977 | Cohen et al. . | |
| 4,167,814 | 9/1979 | Schubert | 433/93 |
| 4,259,067 | 3/1981 | Nelson . | |
| 4,354,837 | 10/1982 | Moore . | |
| 4,883,426 | 11/1989 | Ferrer . | |
| 5,037,298 | 8/1991 | Hickham . | |
| 5,165,891 | 11/1992 | Young . | |
| 5,513,986 | 5/1996 | Feltham et al. . | |
| 5,516,286 | 5/1996 | Kushner | 433/93 |

FOREIGN PATENT DOCUMENTS 220859 4/1942 Switzerland ............................. 433/93

*Primary Examiner*—Nicholas D. Lucchesi
*Attorney, Agent, or Firm*—Jeffrey B. Oster

[57] ABSTRACT

There is disclosed a sterilizeable, disposable or reuseable device comprising a hollow tubular structure configured having a middle protrusion portion having holes drilled therein for tongue retraction and outer wings for mounting cheek retractors, and two cheek retractors positioned for cheek and lip retraction.

5 Claims, 5 Drawing Sheets

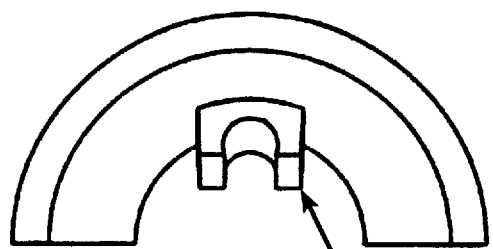
Fig. 5 — SNAP FIT FEATURE
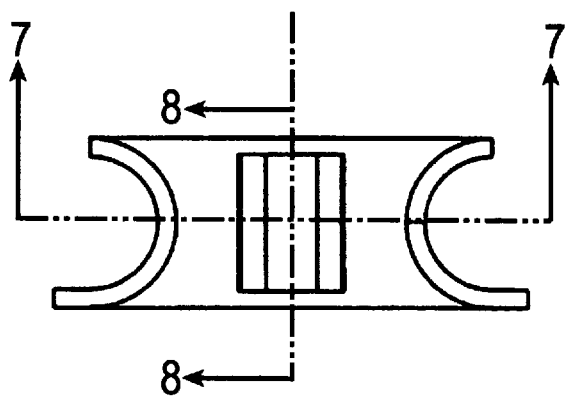
Fig. 6

Section 7-7

Section 8-8

DENTAL APPARATUS TO REMOVE SALIVA WHILE RETRACTING CHEEKS, LIPS AND TONGUE

TECHNICAL FIELD OF THE INVENTION

The present invention provides a sterilizeable, disposable or reuseable device comprising a hollow tubular structure configured having a middle protrusion portion having holes drilled therein for tongue retraction and outer wings for mounting cheek retractors, and two cheek retractors positioned for cheek and lip retraction.

BACKGROUND OF THE INVENTION

During dental procedures, the oral cavity is constantly being filled with body fluids, such as saliva. These fluids can also come from water or other fluids being added to a patient's mouth during a dental procedure. The fluids need to be removed because they could cause problems for any dry field dental procedure and are uncomfortable for the patient. The proximity of the oral soft tissues, such as the tongue, cheek and lip, to the field of work make performing a dry field procedure all the more difficult. Therefore, there is a need in the art to provide such a field for dental automatically in a device that does not require monitoring or manipulation by the practitioner or the necessity for having another person performing retraction or fluid removal procedures while the practitioner is performing the dental procedure.

There are procedures in dentistry that require a dry field across an entire dental arch. Such procedures include, for example, placement of orthodontic brackets, crown work, bridge work and some fluoride treatments.

Saliva collectors have been used in dental procedures. Such devices generally consist of tubing of various sizes and shapes that are connected at one end to a suction device and open at a single opposite end for evacuation of fluids. Such devices generally are positioned near a saliva duct but do not dry and isolate the entire area of a procedure across the entire dental arch. Such tubular devices can sometime further include tissue shields to restrain soft tissue movement in the field of work and they generally pass over the teeth. However, such devices tend to dry only a local area or require human intervention to constantly move such devices to drain more of the mouth. Thus, such devices are uncomfortable for the patient and are inconvenient for the practitioner because of the need to pay attention and move such devices requires time from the practitioner or the constant presence of an assistant. Thus, there is a need in the art to have a device that removes saliva across a wider field automatically without requiring time or attention from the practitioner or an assistant.

Some solutions have involved molding the mouth end (as opposed to the end connected to a vacuum line) of a tubular device to have broader surface area with multiple inlets. Such devices often resemble a flat lollipop-like end on a tube that also have some tongue retraction capabilities but take up a lot of space in a crowded field. Another such device is a hollow tube with two side fins for retracting soft tissue described in U.S. Pat. No. 4,883,426 and one with only one side fin that resembles a golf iron head described in U.S. Pat. No. 4,354,837. In addition, U.S. Patent describes a vacuum head having a valve to prevent backflow when the suction is turned on and off. However, such devices all require constant manipulation by the practitioner or an assistant and are not automatic devices.

Tongue retractors and cheek/lip retractors are also available and generally available and serve their function as separate and discrete items that remain stationary and allow the practitioner to perform the procedure. However such devices still require the use of a separate saliva ejector that needs attention and periodic adjustment.

SUMMARY OF THE INVENTION

The present invention provides a dental device adapted to be placed in the mouth for retracting the cheeks, lips and tongue, comprising:

(a) a tubular element having a predominantly rigid, yet partially flexible structure that retains it configuration, having one end of the tubular element adapted for connection to a vacuum line and having the opposite end closed, and having walls surrounding a hollow space interior, wherein the vacuum end and the opposite end point in a forward direction, wherein the tubular element is shaped with (i) a loop means for retracting the tongue wherein the loop means extends in a downward direction when inserted into the mouth, and (ii) two parallel bends in a forward direction at from 45 degree to about 120 degrees, at each end of the tube, for attachment of cheek retractor elements, and wherein the tubular element further comprises a plurality of small holes drilled through the wall of the tubular element in the forward direction; and (b) two cheek retractor means, having opposite orientations, attached at or near the bends of the tubular element.

Preferably, the loop means for retracting the tongue protrudes in a downward direction a distance of from about 1 cm to about 5 cm. Preferably, the loop means have a plurality of holes in the tubular element having a forward orientation. Preferably, the tubular element is made from a rigid clear plastic and having a circular shape. Preferably, the cheek retractors attach to the tubular element by a snap-on means.

BRIEF DESCRIPTION OF THE DRAWINGS

FIG. 1 shows two cheek cups or cheek retractor means that attach to the tubular element.

FIG. 5 shows a preferred cheek retractor means having a snap-on fit means for a circular tubular element.

FIG. 6 shows an elevational view of the cheek retractor means shown in FIG. 5.

DETAILED DESCRIPTION OF THE INVENTION

Figure 1:
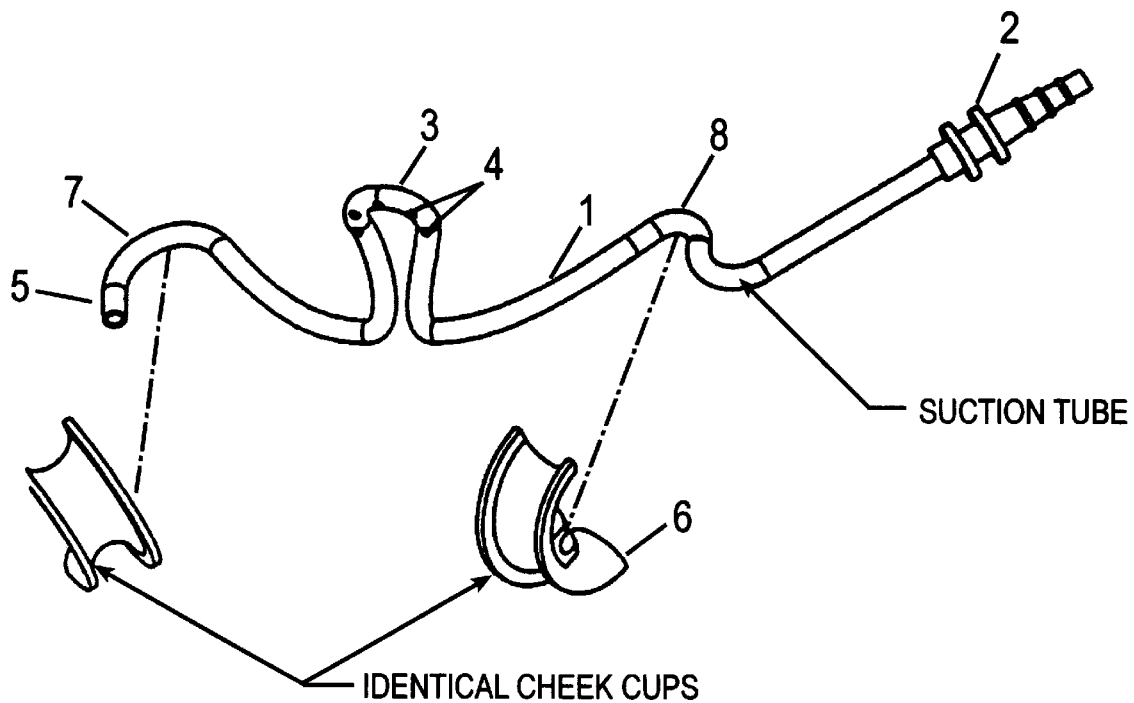
FIG. 1 shows a schematic drawing (front, upside down view) of the inventive dental device showing the tubular element shaped with a loop means, wherein the loop means contains five holes.
Figure 2:
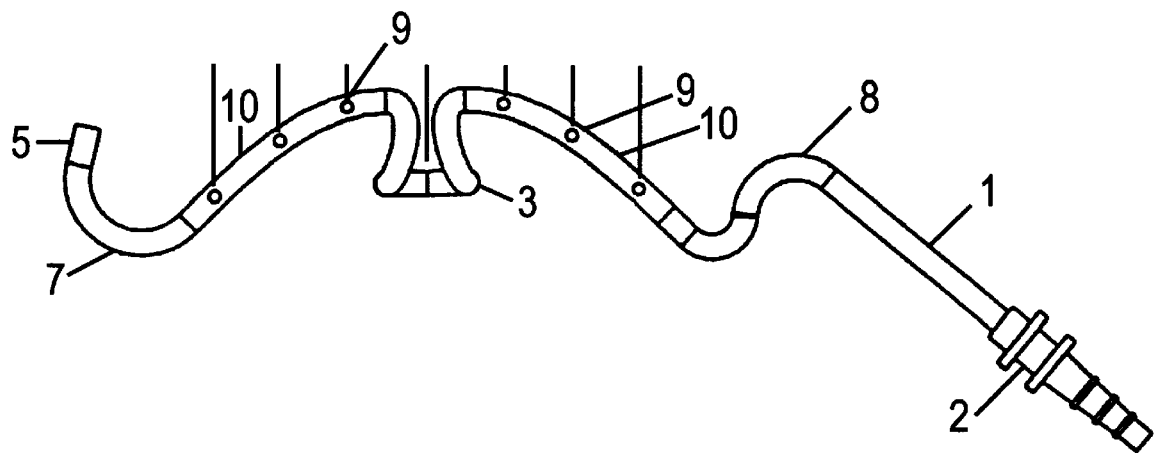
FIG. 2 shows a top view of the tubular element showing the bending of the tubular element and having six holes having an upward orientation, three on either side of the loop element.

The present invention provides a dental device adapted to be placed in the mouth for retracting the cheeks, lips and tongue, comprising:

(a) a tubular element having a predominantly rigid, yet partially flexible structure that retains it configuration, having one end of the tubular element adapted for connection to a vacuum line and having the opposite end closed, and having walls surrounding a hollow space interior, wherein the vacuum end and the opposite end point in a forward direction, wherein the tubular element is shaped with (i) a loop means for retracting the tongue wherein the loop means extends in a downward direction when inserted into the mouth, and (ii) two parallel bends in a forward direction at from 45 degree to about 120 degrees, at each end of the tube, for attachment of cheek retractor elements, and wherein the tubular element further comprises a plurality of small holes drilled through the wall of the tubular element in the forward direction; and (b) two cheek retractor means, having opposite orientations, attached at or near the bends of the tubular element.

Preferably, the loop means for retracting the tongue protrudes in a downward direction a distance of from about 1 cm to about 5 cm. Preferably, the loop means have a plurality of holes in the tubular element having a forward orientation. Preferably, the tubular element is made from a rigid clear plastic and having a circular shape. Preferably, the cheek retractors attach to the tubular element by a snap-on means.

The inventive dental device is adapted to fit in a person's mouth and be composed or a rigid material that retains its basic shape yet provides some flexibility to bend to fit into a mouth of different size without breaking. Preferred materials for the tubular element are plastics, preferably food grade plastics that can be sterilized by conventional means of sterilization (e.g., heat ethylene oxide, hydrogen peroxide, ionizing radiation). Such plastics or polymeric materials, include, but are not limited to polyethylene, polypropylene, polycarbonate, polyethylenetetraphalic glycol (PETG), polyethylethylenetetraphalate (PET), or combinations thereof. Most preferably the tubular element is made from PETG. In addition, the cheek retractor means is made from, for example, nylon or azylonitrile butadiene styrene (ABS) or other suitable polymeric material that also can be used for food packaging.

The inventive dental device comprises a tubular element (1) and two cheek retractor means (6). The dental device may optionally further comprise a vacuum tube adapter (2). The tubular element (1) is configured to have a closed end (5) and an open end (2) which may or may not further contain a vacuum tube adapter for attaching the open end of the tubular element to a vacuum line for ejecting saliva.

Figure 3:
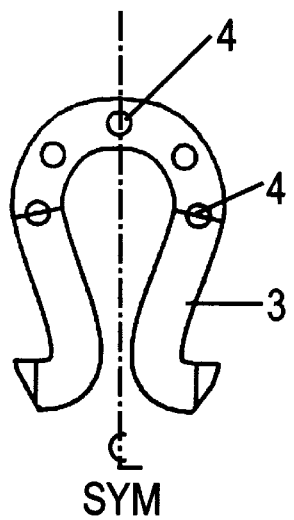
FIG. 3 shows a close up view of the loop element having five holes each with a forward orientation.
Figure 4:
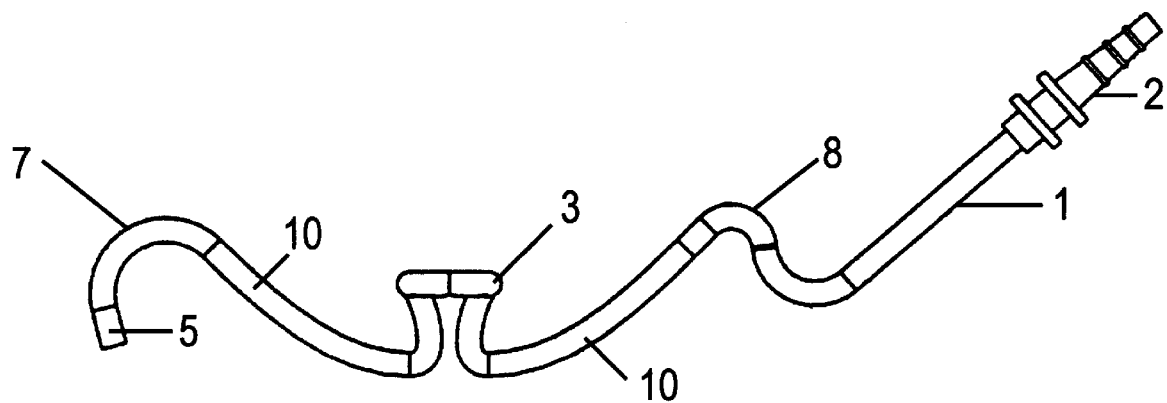
FIG. 4 shows a bottom view of the tubular element without holes having a bottom orientation and showing the preferred bend at for attaching the cheek retractor means at the end closer to the open end of the tube, which further shows a vacuum tube adapter means.
Figure 7:
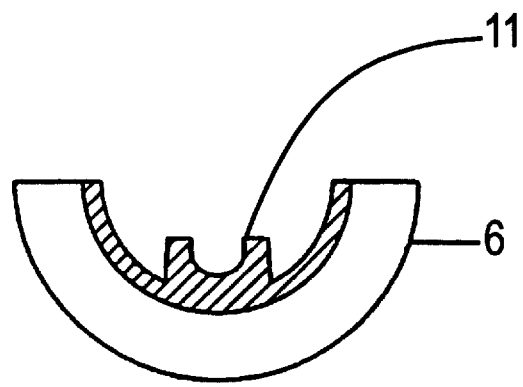
FIG. 7 shows a sectional view of the cheek retractor means taken along section line 7—7 in FIG. 6.
Figure 8:
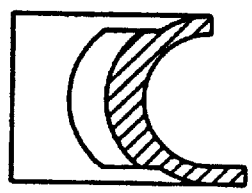
FIG. 8 shows a sectional view of the cheek retractor means taken along section line 8—8 in FIG. 6.

The tubular element contains a loop means (3) for retracting the tongue that preferably contains holes (4) oriented such that the holes will point away from the tongue (otherwise the holes will be plugged up by the tongue). Preferably, the holes are provided in a symmetrical pattern on the loop means as shown in FIG. 3.

The tubular element further comprises two bends for attaching the cheek retractor means in opposite orientations, wherein one bend (7) is located adjacent to the closed end (5) and is called the closed end bend, and the other bend (8) is located adjacent to the open end of the tubular element (open end bend). The open end bend provides for a means for attaching the cheek retractor element and to orient the open end (with or without a further vacuum line adapter means) such that the open end is accessible outside of the patient's mouth. Preferably the portions of the tubular element located between the loop means (3) and both the open end bend and the closed end bend (10) contains holes (9) that will have a upward orientation when inserted in the patient's mouth. The length of the tubular means (10) should be approximately the length of a radius of the dental arch or approximately half of the width of a mouth, fully stretched for the dental procedure. This length will be from about 6 cm to about 18 cm. Most preferably, the length of the bent tubular element is approximately 12 cm to fit an average adult mouth.

The cheek retractor means (6) is shown as a preferred embodiment in FIGS. 5 through 8 in each of four orientations. The preferred cheek retractor means further comprises a means for attaching the cheek retractor means to the open end bend (8) and the closed end bend (7) of the tubular element (11). The preferred means for attaching shown in FIGS. 5 through 8 is a snap-on means for a circular tubular element.

I claim:

1. A dental device adapted to be placed in the mouth for retracting the cheeks, lips and tongue, comprising:

(a) a tubular element having a predominantly rigid, yet partially flexible structure that retains its configuration, one end of the tubular element adapted for connection to a vacuum line and the opposite end closed, and having walls surrounding a hollow space interior, wherein the vacuum end and the opposite end point in a forward direction, wherein the tubular element is shaped with (i) a loop means for retracting the tongue wherein the loop means extends in a downward direction when inserted into the mouth, and (ii) two parallel bends in a forward direction at from 45 degrees to about 120 degrees, at each end of the tube, for attachment of cheek retractor elements, and wherein the tubular element further comprises a plurality of small holes drilled through the wall of the tubular element in the forward direction; and (b) two cheek retractor means, having opposite orientations, attached at or near the bends of the tubular element.

2. The dental device of claim 1 wherein the loop means for retracting the tongue protrudes in a downward direction a distance of from about 1 cm to about 5 cm.

3. The dental device of claim 1 wherein the loop means have a plurality of holes in the tubular element having a forward orientation.

4. The dental device of claim 1 wherein the tubular element is made from a rigid clear plastic and has a circular shape.

5. The dental device of claim 1 wherein the cheek retractor means attach to the tubular element by a snap-on means.

* * * * *